US011134863B2

(12) United States Patent
Penta et al.

(10) Patent No.: US 11,134,863 B2
(45) Date of Patent: Oct. 5, 2021

(54) GENERATING ORTHOTIC PRODUCT RECOMMENDATIONS

(71) Applicant: Scholl's Wellness Company LLC, Boston, MA (US)

(72) Inventors: Rama Penta, Whippany, NJ (US); Harold Howlett, Whippany, NJ (US); Steven Dawson, Whippany, NJ (US); Dmitri Svistula, Whippany, NJ (US); Alan Shimoide, Whippany, NJ (US); Charles Fletcher, Whippany, NJ (US)

(73) Assignee: Scholl's Wellness Company LLC, Parsippany, NJ (US)

( * ) Notice: Subject to any disclaimer, the term of this patent is extended or adjusted under 35 U.S.C. 154(b) by 434 days.

(21) Appl. No.: 15/765,718

(22) PCT Filed: Oct. 5, 2016

(86) PCT No.: PCT/US2016/055607
§ 371 (c)(1),
(2) Date: Apr. 3, 2018

(87) PCT Pub. No.: WO2017/062530
PCT Pub. Date: Apr. 13, 2017

(65) Prior Publication Data
US 2018/0279912 A1    Oct. 4, 2018

Related U.S. Application Data

(60) Provisional application No. 62/237,520, filed on Oct. 5, 2015.

(51) Int. Cl.
*A61B 5/107* (2006.01)
*G01B 11/24* (2006.01)
(Continued)

(52) U.S. Cl.
CPC ........... *A61B 5/1074* (2013.01); *A43D 1/02* (2013.01); *A43D 1/025* (2013.01); *A61B 5/0064* (2013.01);
(Continued)

(58) Field of Classification Search
None
See application file for complete search history.

(56) References Cited

U.S. PATENT DOCUMENTS 1,281,987 A    10/1918   McSweeney
2,043,187 A    6/1936    Owens
(Continued)

FOREIGN PATENT DOCUMENTS

CA    1249929 A    2/1989
CA    2324967 A1   5/2002
(Continued)

OTHER PUBLICATIONS

"Extended European Search Report from EP Application No. 16854268", dated Mar. 15, 2019.
(Continued)

*Primary Examiner* — Jiangeng Sun
(74) *Attorney, Agent, or Firm* — Lowenstein Sandler LLP

(57) ABSTRACT

A method to generate orthotic product recommendations for users includes receiving interactions from a user including identification of one or more extremity areas of the user's body, the one or more extremity areas relevant to selection of one or more orthotic products. On-screen cues and interactions are provided to assist in positioning of the one or more extremity areas relative to one or more imaging sensors. Scan data is received from the one or more imaging sensors. A model of the one or more extremity areas is generated based on the scan data including estimating one or more complete circumferences of the one or more extremity (Continued)

areas. One or more orthotic products are identified based on a comparison of the model of the one or more extremity areas and one or more factors associated with the user and a plurality of orthotic products. A recommendation is provided that includes the one or more orthotic products.

9 Claims, 7 Drawing Sheets

(51) Int. Cl.
    *A61B 5/00*     (2006.01)
    *A61B 5/103*     (2006.01)
    *A43D 1/02*     (2006.01)
    *G01G 19/50*     (2006.01)
    *A61F 5/01*     (2006.01)
    *G01G 19/414*     (2006.01)

(52) U.S. Cl.
    CPC ............ *A61B 5/107* (2013.01); *A61B 5/1036* (2013.01); *A61B 5/1072* (2013.01); *A61B 5/706* (2013.01); *G01B 11/24* (2013.01); *A61F 5/01* (2013.01); *G01G 19/4144* (2013.01); *G01G 19/50* (2013.01)

(56) References Cited

U.S. PATENT DOCUMENTS

| | | |
|---|---|---|
| 2,055,072 A | 9/1936 | Everston |
| 2,063,625 A | 12/1936 | Rigandi |
| 2,107,620 A | 2/1938 | Rigandi |
| 2,157,026 A | 5/1939 | Sochor |
| 2,221,202 A | 11/1940 | Ratcliff |
| 2,446,448 A | 8/1948 | Whitman |
| 2,447,954 A | 8/1948 | Meldman |
| 2,464,023 A | 3/1949 | Carson |
| 2,863,231 A | 12/1958 | Jones |
| 2,975,519 A | 3/1961 | Berlin, Jr. et al. |
| 3,066,417 A | 12/1962 | Samuels |
| 3,233,348 A | 2/1966 | Gilkerson |
| 3,328,882 A | 7/1967 | Blivice |
| 3,375,586 A | 4/1968 | Kennedy |
| 3,398,469 A | 8/1968 | Bressan |
| 3,457,647 A | 7/1969 | David et al. |
| 3,696,456 A | 10/1972 | Tom et al. |
| 3,828,792 A | 8/1974 | Valenta |
| 3,859,740 A | 1/1975 | Kemp |
| 4,124,946 A | 11/1978 | Tomlin |
| 4,168,585 A | 9/1979 | Gleichner |
| 4,267,728 A | 5/1981 | Manley et al. |
| 4,408,402 A | 10/1983 | Looney |
| 4,412,364 A | 11/1983 | Orea Mateo |
| 4,430,645 A | 2/1984 | Eskandry et al. |
| 4,449,264 A | 5/1984 | Schwartz |
| 4,494,321 A | 1/1985 | Lawlor |
| 4,510,636 A | 4/1985 | Phillips |
| 4,510,700 A | 4/1985 | Brown |
| 4,517,696 A | 5/1985 | Schartz |
| 4,520,581 A | 6/1985 | Irwin et al. |
| 4,538,353 A | 9/1985 | Gardner |
| 4,555,696 A | 11/1985 | Brown |
| 4,597,196 A | 7/1986 | Brown |
| 4,604,807 A | 8/1986 | Bock et al. |
| 4,648,923 A | 3/1987 | Chapnick |
| 4,656,344 A | 4/1987 | Mergenthaler et al. |
| 4,686,993 A | 8/1987 | Grumbine |
| 4,688,338 A | 8/1987 | Brown |
| 4,702,255 A | 10/1987 | Schenkl |
| 4,745,290 A | 5/1988 | Frankel et al. |
| D296,493 S | 7/1988 | Diaz |
| 4,760,654 A | 8/1988 | Limbach |
| 4,782,605 A | 11/1988 | Chapnick |
| 4,823,420 A | 4/1989 | Bartneck |
| 4,858,621 A | 8/1989 | Franks |
| RE33,066 E | 9/1989 | Stubblefield |
| 4,876,758 A | 10/1989 | Rolloff et al. |
| 4,901,390 A | 2/1990 | Daley |
| 4,917,105 A | 4/1990 | Tiitola et al. |
| 4,962,593 A | 10/1990 | Brown |
| 4,972,718 A | 11/1990 | Said et al. |
| 5,014,706 A | 5/1991 | Philipp |
| 5,015,427 A | 5/1991 | Sosnow |
| 5,025,476 A | 6/1991 | Gould et al. |
| 5,068,983 A | 12/1991 | Marc |
| 5,077,915 A | 1/1992 | Gross |
| 5,092,060 A | 3/1992 | Frachey et al. |
| 5,128,880 A | 7/1992 | White |
| 5,164,793 A | 11/1992 | Wolfersberger et al. |
| 5,168,634 A | 12/1992 | Misevich |
| 5,170,572 A | 12/1992 | Kantro |
| 5,175,946 A | 1/1993 | Tsai |
| 5,195,030 A | 3/1993 | White |
| 5,203,096 A | 4/1993 | Rosen |
| 5,206,804 A | 4/1993 | Thies et al. |
| 5,212,894 A | 5/1993 | Paparo |
| 5,216,594 A | 6/1993 | White et al. |
| 5,237,520 A | 8/1993 | White |
| 5,282,326 A | 2/1994 | Schroer, Jr. et al. |
| 5,299,454 A | 4/1994 | Fuglewicz et al. |
| 5,311,677 A | 5/1994 | Mann et al. |
| 5,317,819 A | 6/1994 | Ellis, III |
| 5,339,252 A | 8/1994 | White et al. |
| 5,341,819 A | 8/1994 | Hyvarinen |
| 5,361,133 A | 11/1994 | Brown et al. |
| 5,369,896 A | 12/1994 | Frachey et al. |
| 5,394,624 A | 3/1995 | Siepser |
| D357,349 S | 4/1995 | Vasyli |
| D358,249 S | 5/1995 | Vasyli |
| 5,435,077 A | 7/1995 | Pyle |
| 5,438,768 A | 8/1995 | Bauerfeind |
| D367,164 S | 2/1996 | Fisher et al. |
| 5,542,196 A | 8/1996 | Kantro |
| 5,586,067 A | 12/1996 | Gross et al. |
| 5,611,153 A | 3/1997 | Fisher et al. |
| 5,640,779 A | 6/1997 | Rolloff et al. |
| 5,659,395 A | 8/1997 | Brown et al. |
| 5,671,055 A | 9/1997 | Whittlesey et al. |
| 5,671,362 A | 9/1997 | Cowe et al. |
| 5,746,011 A | 5/1998 | Hedstroem |
| 5,790,256 A | 8/1998 | Brown et al. |
| 5,822,873 A | 10/1998 | Meilman |
| 5,918,383 A | 7/1999 | Chee |
| 5,933,984 A | 8/1999 | Carlson et al. |
| 5,945,610 A | 8/1999 | Galasso |
| 5,951,935 A | 9/1999 | Healy et al. |
| 5,957,870 A | 9/1999 | Yamato et al. |
| 5,979,067 A | 11/1999 | Waters |
| 5,987,982 A | 11/1999 | Wenman et al. |
| 5,989,700 A | 11/1999 | Krivopal |
| 6,000,147 A | 12/1999 | Kellerman |
| 6,038,793 A | 3/2000 | Kendall |
| 6,041,521 A | 3/2000 | Wong |
| 6,041,524 A | 3/2000 | Brooks |
| 6,098,319 A | 8/2000 | Epstein |
| 6,125,557 A | 10/2000 | Brown |
| 6,131,311 A | 10/2000 | Brown et al. |
| 6,145,220 A | 11/2000 | Johnson, Jr. et al. |
| 6,160,264 A | 12/2000 | Rebiere |
| 6,163,971 A | 12/2000 | Humphries, Jr. et al. |
| 6,219,929 B1 | 4/2001 | Tasker et al. |
| 6,233,847 B1 | 5/2001 | Brown |
| 6,247,250 B1 | 6/2001 | Hauser |
| 6,269,555 B1 | 8/2001 | Brown |
| 6,282,816 B1 | 9/2001 | Rosendahl |
| 6,286,232 B1 | 9/2001 | Snyder et al. |
| 6,289,107 B1 | 9/2001 | Borchers et al. |
| 6,301,805 B1 | 10/2001 | Howlett et al. |
| 6,301,807 B1 | 10/2001 | Gardiner |
| 6,315,786 B1 | 11/2001 | Smuckler |
| 6,331,893 B1 | 12/2001 | Brown et al. |
| 6,345,455 B1 | 2/2002 | Greer, Jr. et al. |
| 6,408,543 B1 | 6/2002 | Erickson et al. |
| 6,430,831 B1 | 8/2002 | Sundman |

(56) References Cited

U.S. PATENT DOCUMENTS

| | | |
|---|---|---|
| 6,481,120 B1 | 11/2002 | Xia et al. |
| 6,498,590 B1 | 12/2002 | Dietz et al. |
| 6,505,522 B1 | 1/2003 | Wilssens |
| 6,508,017 B1 | 1/2003 | Debarro et al. |
| 6,519,874 B1 | 2/2003 | Dean |
| 6,532,299 B1 | 3/2003 | Sachdeva et al. |
| 6,550,149 B2 | 4/2003 | Dowdell |
| 6,557,273 B2 | 5/2003 | Polifroni |
| 6,560,902 B1 | 5/2003 | Eschweiler |
| 6,563,423 B2 | 5/2003 | Smith |
| 6,564,465 B1 | 5/2003 | Ward |
| D475,184 S | 6/2003 | Polifroni |
| 6,585,328 B1 | 7/2003 | Oexman et al. |
| 6,594,922 B1 | 7/2003 | Mansfield et al. |
| 6,598,321 B2 | 7/2003 | Crane et al. |
| 6,601,320 B1 | 8/2003 | Brown |
| 6,604,301 B1 | 8/2003 | Manoli, II et al. |
| 6,611,195 B1 | 8/2003 | Manneschi et al. |
| 6,618,960 B2 | 9/2003 | Brown |
| 6,691,432 B2 | 2/2004 | Masseron |
| 6,802,138 B2 | 10/2004 | McManus et al. |
| 6,804,571 B2 | 10/2004 | Fullen et al. |
| 6,823,550 B2 | 11/2004 | Kantro |
| 6,845,568 B2 | 1/2005 | Ward |
| 6,854,199 B2 | 2/2005 | Polifroni |
| 6,909,373 B2 | 6/2005 | Power et al. |
| 6,931,763 B2 | 8/2005 | Bray et al. |
| 6,939,502 B2 | 9/2005 | Lyden |
| 6,954,557 B2 | 10/2005 | Kim et al. |
| 6,964,205 B2 | 11/2005 | Papakostas et al. |
| 7,089,152 B2 | 8/2006 | Oda et al. |
| 7,100,296 B2 | 9/2006 | Root |
| 7,120,958 B2 | 10/2006 | Copeskey et al. |
| 7,421,808 B2 | 9/2008 | Baier et al. |
| 7,484,319 B2 | 2/2009 | Cheskin et al. |
| 7,599,933 B2 | 10/2009 | Domany et al. |
| 7,617,068 B2 | 11/2009 | Tadin et al. |
| 7,707,751 B2 | 5/2010 | Avent et al. |
| 7,742,633 B2 | 6/2010 | Huang et al. |
| 7,789,840 B2 | 9/2010 | Nole |
| 7,914,014 B1 | 3/2011 | Robinson |
| 7,958,653 B2 | 6/2011 | Howlett et al. |
| 8,117,922 B2 | 2/2012 | Xia et al. |
| 8,170,705 B2 | 5/2012 | Koelling et al. |
| 8,406,454 B2 | 3/2013 | Bar |
| 8,479,416 B2 | 7/2013 | Auger et al. |
| 8,578,634 B1 | 11/2013 | Nguyen et al. |
| 8,800,169 B2 | 8/2014 | Howlett et al. |
| 9,002,426 B2 | 4/2015 | Quaid et al. |
| 9,038,482 B2 | 5/2015 | Xia et al. |
| 9,576,311 B2 | 2/2017 | Xia et al. |
| 2002/0050080 A1 | 5/2002 | Vasyli |
| 2002/0056208 A1 | 5/2002 | Brown |
| 2002/0060630 A1 | 5/2002 | Power |
| 2002/0071597 A1 | 6/2002 | Ravitz et al. |
| 2002/0083618 A1 | 7/2002 | Erickson et al. |
| 2003/0009915 A1 | 1/2003 | Bacon |
| 2003/0061733 A1 | 4/2003 | Karsten |
| 2003/0079303 A1 | 5/2003 | Kantro |
| 2003/0140523 A1 | 7/2003 | Issler |
| 2003/0164954 A1 | 9/2003 | Gerhard et al. |
| 2004/0020078 A1 | 2/2004 | Bray et al. |
| 2004/0025376 A1 | 2/2004 | Grisoni et al. |
| 2004/0032052 A1 | 2/2004 | Meyers et al. |
| 2004/0143452 A1 | 7/2004 | Pattillo et al. |
| 2004/0168329 A1 | 9/2004 | Ishimaru |
| 2004/0181976 A1 | 9/2004 | Copeskey et al. |
| 2004/0194344 A1 | 10/2004 | Tadin |
| 2004/0221487 A1 | 11/2004 | Fried |
| 2004/0250359 A1 | 12/2004 | Spivey |
| 2004/0260508 A1 | 12/2004 | Pattillo et al. |
| 2005/0028109 A1 | 2/2005 | Richards et al. |
| 2005/0030372 A1 | 2/2005 | Jung et al. |
| 2005/0044751 A1 | 3/2005 | Alaimo et al. |
| 2005/0049816 A1 | 3/2005 | Oda et al. |
| 2005/0066545 A1 | 3/2005 | Peoples |
| 2005/0072892 A1 | 4/2005 | Fell |
| 2005/0108899 A1 | 5/2005 | Kielt et al. |
| 2005/0203712 A1 | 9/2005 | Lowe |
| 2005/0223604 A1 | 10/2005 | Neuner |
| 2005/0262733 A1 | 12/2005 | Dean |
| 2006/0098896 A1 | 5/2006 | Pishdadian et al. |
| 2007/0011173 A1 | 1/2007 | Agostino |
| 2007/0043582 A1 | 2/2007 | Peveto et al. |
| 2007/0107261 A1 | 5/2007 | Cheskin et al. |
| 2007/0202478 A1 | 8/2007 | Al-Obaidi et al. |
| 2007/0253004 A1 | 11/2007 | Danenberg et al. |
| 2007/0289170 A1 | 12/2007 | Avent et al. |
| 2008/0072461 A1 | 3/2008 | Howlett et al. |
| 2008/0083416 A1 | 4/2008 | Xia et al. |
| 2008/0097720 A1 | 4/2008 | Tadin et al. |
| 2008/0196273 A1 | 8/2008 | Kosta |
| 2008/0292179 A1 | 11/2008 | Busch |
| 2009/0076772 A1 | 3/2009 | Hinshaw et al. |
| 2009/0240514 A1 | 9/2009 | Oexman et al. |
| 2009/0312626 A1 | 12/2009 | Hanrahan et al. |
| 2010/0269371 A1 | 10/2010 | Gray |
| 2011/0028877 A1 | 2/2011 | Vollbrecht et al. |
| 2011/0247235 A1 | 10/2011 | De et al. |
| 2011/0317871 A1* | 12/2011 | Tossell .............. G06K 9/00369 382/103 |
| 2012/0056800 A1* | 3/2012 | Williams ............. G06F 3/0304 345/156 |
| 2012/0162065 A1 | 6/2012 | Tossell et al. |
| 2012/0185094 A1* | 7/2012 | Rosenstein .......... G05D 1/0251 700/259 |
| 2012/0197464 A1* | 8/2012 | Wang .................. G05D 1/0038 701/2 |
| 2012/0260525 A1 | 10/2012 | Kim |
| 2012/0276999 A1 | 11/2012 | Kalpaxis et al. |
| 2013/0053677 A1 | 2/2013 | Schoenfeld |
| 2013/0172787 A1 | 7/2013 | Marovets |
| 2014/0107967 A1 | 4/2014 | Xia et al. |
| 2014/0107968 A1 | 4/2014 | Xia et al. |
| 2014/0195297 A1 | 7/2014 | Abuelsaad et al. |
| 2014/0309534 A1 | 10/2014 | Pichler et al. |
| 2014/0334670 A1* | 11/2014 | Guigues ................ G06K 9/469 382/103 |
| 2015/0223730 A1 | 8/2015 | Ferrantelli et al. |
| 2015/0238098 A1 | 8/2015 | Park et al. |

FOREIGN PATENT DOCUMENTS

| | | |
|---|---|---|
| CA | 2663532 A1 | 3/2008 |
| CA | 2811132 A1 | 3/2008 |
| CN | 2389537 Y | 8/2000 |
| CN | 1344907 A | 4/2002 |
| CN | 2707063 Y | 7/2005 |
| DE | 19923280 A1 | 11/1999 |
| DE | 20119402 U1 | 1/2002 |
| EP | 0119660 A1 | 9/1984 |
| EP | 0173396 A2 | 3/1986 |
| EP | 0534503 B1 | 9/1997 |
| FR | 2776175 A1 | 9/1999 |
| GB | 2349728 A | 11/2000 |
| JP | H03247305 A | 11/1991 |
| JP | H03251203 A | 11/1991 |
| JP | H0518810 A | 1/1993 |
| JP | 2005192744 A | 7/2005 |
| JP | 2007275307 A | 10/2007 |
| JP | 2014179092 A | 9/2014 |
| NL | 9100591 A | 11/1992 |
| SU | 1814877 | 3/1991 |
| TW | 440836 B | 6/2001 |
| TW | 200525400 A | 8/2005 |
| WO | 9723769 A1 | 7/1997 |
| WO | 02052918 A2 | 7/2002 |
| WO | 03037124 A1 | 5/2003 |
| WO | 2008036397 A2 | 3/2008 |
| WO | 2008036398 A3 | 10/2008 |
| WO | 2014037939 A1 | 3/2014 |

(56) References Cited

FOREIGN PATENT DOCUMENTS

| WO | 2015001416 A1 | 1/2015 | |
|---|---|---|---|
| WO | 2015157581 A1 | 10/2015 | |
| WO | WO-2015157581 A1 * | 10/2015 | ............ A61B 5/1072 |

OTHER PUBLICATIONS

"Men's Sizing Charts", https://web.archive.org/web/20141114130834/https://www.tommiecopper.com/mens-sizing-charts/, retrieved on Mar. 6, 2019.

Cavanaugh; et al., "The Arch Index: A Useful Measure From Footprints", Journal of Biomechanics, Jan. 1987, vol. 20 No. 5, 547-551.

Chu; et al., "The Use of Arch Index to Characterize Arch Height: A Digital Image Processing Approach", IEEE Transactions on Biomedical Engineering, Nov. 1995, vol. 42 No. 11, 1088-1093.

Davis; et al., "Decomposition of Superimposed Ground Reaction Forces into Left and Right Force Profiles", Journal of Biomechanics, Apr. 1993, vol. 26 No. 4-5, 593-597.

"European Search Report for Application No. EP10171065 dated Aug. 27, 2010".

"European Search Report for Application No. EP11192770 dated Feb. 10, 2012".

"European Search Report for Application No. EP11192771 dated Feb. 10, 2012".

"European Search Report for Application No. EP11192772 dated Feb. 10, 2012".

"International Search Report for International Application No. PCT/US2015/025211 filed Apr. 9, 2015".

International Search Report for PCT/US2007/020475 (dated Apr. 29, 2008)—6 Pages.

McPoil; et al., "Relationship Between Three Static Angles of the Rearfoot and the Pattern of Rearfoot Motion During Walking", Journal of Orthopaedic & Sports Physical Therapy, Jun. 1996, vol. 23 No. 6, 370-375.

Menz; Hylton B., "Alternative Techniques for the Clinical Assessment of Foot Pronation", Journal of the American Podiatric Medical Association, Mar. 1998, vol. 88 No. 3, 119-129.

PCT Search Report for International Application No. PCT/US2007/020476 dated Sep. 4, 2008, Tobias Gorlach.

ROC (Taiwan) Search Report dated Apr. 24, 2014, Translation; 1 page

ROC (Taiwan) Search Report (Englilsh Translation) dated Mar. 19, 2014 for ROC (Taiwan) Patent Application No. 102123875; 1 page . . . .

Torburn; et al., "Assessment of Rearfoot Motion: Passive Positioning, One-Legged Standing, Gait", Foot & Ankle International, Oct. 1998, vol. 19 No. 10, 688-693.

Urry; et al., "Arch Indexes from Ink Footprints and Pressure Platforms are Different", The Foot, Jun. 2005, vol. 15 No. 2, 68-73.

Written Opinion for PCT/US2007/020475 (Filing Date Sep. 21, 2007)—10 Pages . . . .

Wrobel; et al., "Reliability and Validity of Current Physical Examination Techniques for the Foot and Ankle", Journal of the American Podiatric Medical Association, May 2008, vol. 98 No. 3, 197-206.

\* cited by examiner

700

GENERATING ORTHOTIC PRODUCT RECOMMENDATIONS

BACKGROUND

Conventional orthotic products for upper and lower extremities, such as elbow braces, arm braces, forearm-wrist braces, forearm-wrist-thumb braces, forearm-wrist-hand braces, knee braces, ankle braces, and the like, may be sold from retail displays. The orthotic products may include packaging that provides some guidance, such as a description of a type of arch support provided by an orthotic product. However, if a user does not know how much arch support is needed, this type of guidance is not helpful. This uncertainty may result in the customer buying multiple orthotic products before the customer finally finds the orthotic product that meets the customer's needs.

Devices exist that generate three-dimensional models of the users using full-body scans of the users. These devices are problematic for several reasons. First, the scans may be inaccurate because the users move around and their positioning may not be able to be precisely controlled. Second, the steps employed for getting a user to turn around to get the full-body scans may be so complicated that users become irritated and/or give up before receiving a recommendation. Third, to support a full-body scan, the size of a device may be so large that the device may not fit in a retailer's store. Similarly, the cost of the hardware for the device that performs a full-body scan may be prohibitively expensive.

SUMMARY

Embodiments generally relate to generating orthotic product recommendations for users. In some embodiments, a method to generate orthotic product recommendations for users includes receiving interactions from a user including identification of one or more extremity areas of the user's body, the one or more extremity areas relevant to selection of one or more orthotic products. On-screen cues and interactions are provided to assist in positioning of the one or more extremity areas relative to one or more imaging sensors. Scan data is received from the one or more imaging sensors. A model of the one or more extremity areas is generated based on the scan data including estimating one or more complete circumferences of the one or more extremity areas. One or more orthotic products are identified based on a comparison of the model of the one or more extremity areas and one or more factors associated with the user and a plurality of orthotic products. A recommendation is provided that includes the one or more orthotic products.

The scan data may include images of a front of the user and estimating the one or more complete circumferences of the one or more extremity areas may include determining a shape of the one or more extremity areas that is not visible from the images. The one or more factors may include a body mass index of the user. Providing the on-screen cues and interactions may include receiving the scan data from the one or more imaging sensors, wherein the scan data is of a leg that includes a knee, determining whether the leg is correct, responsive to determining that the leg is correct, determining whether the knee is visible, and responsive to the knee being visible, determining whether the leg is in a first position. If the leg is incorrect, the knee is not visible, or the leg is in a second position, the user may be instructed to make a modification. The knee may not be visible because a garment obstructs part of the knee. Providing the user with the recommendation may include emailing the recommendation to an email address of the user.

Generating the model may include performing cloud-point segmentation to divide the scan data into point clusters, identifying a point-cluster centroid for each of the point clusters, identifying locations of joints in the leg based on the point-cluster centroids, generating a two-dimensional depth map of the leg based on the locations of the joints, generating a point cloud of the leg based on the two-dimensional depth map, determining one or more partial circumferences that correspond to one or more points of the leg from the point cloud, and determining the one or more complete circumferences based on the one or more partial circumferences. The one or more complete circumferences may have an ovoid shape.

In some embodiments, a kiosk includes a display configured to receive interactions from a user including identification of one or more extremity areas of the user's body, the one or more extremity areas relevant to selection of one or more orthotic products and configured to provide on-screen cues and interactions to assist in positioning of a foot of the user on one or more of a foot mat and an elevated foot platform relative to one or more imaging sensors. The kiosk may also include a foot mat configured to sense pressure of the foot of a user. The kiosk may also include an elevated foot platform that reduces or prevents rotational movement of the foot of the user. The kiosk may also include one or more imaging sensors configured to capture scan data of the user. The kiosk may also include one or more processors coupled to a memory, a modelling engine stored on the memory and configured to generate a model of the one or more extremity areas based upon the scan data, the model including one or more estimated ovoid shapes of the one or more extremity areas and a product user interface module stored on the memory and configured to identify the one or more orthotic products for the user based on comparing the model of the one or more extremity areas to parameters associated with a plurality of orthotic products, where the display provides the user with a recommendation that includes the one or more orthotic products.

Other aspects may include corresponding methods, systems, apparatus, and computer program products.

The system and methods described below advantageously provide accurate scan data because the user is confined to specific positions and guided through the process with an easy-to-use system. Next, because the scan data is all captured from a forward-facing user, the process is simple and quick. Another advantage includes that because the imaging sensors capture scan data from one direction, the kiosk is a reasonable size that may fit in retail stores. Lastly, the kiosk uses off-the-shelf low cost hardware that reduces the overall price of the kiosk.

BRIEF DESCRIPTION OF THE DRAWINGS

The disclosure is illustrated by way of example, and not by way of limitation in the figures of the accompanying drawings in which like reference numerals are used to refer to similar elements.

DETAILED DESCRIPTION

While methods, apparatuses, and computer-readable media are described herein by way of examples and embodiments, those skilled in the art recognize that methods, apparatuses, and computer-readable media for generating an orthotic product recommendation are not limited to the embodiments or drawings described. It should be understood that the drawings and description are not intended to be limited to the particular form disclosed. Rather, the intention is to cover all modifications, equivalents, and alternatives falling within the spirit and scope of the appended claims. Any headings used herein are for organizational purposes only and are not meant to limit the scope of the description or the claims. As used herein, the word "may" is used in a permissive sense (i.e., meaning having the potential to) rather than the mandatory sense (i.e., meaning must). Similarly, the words include," "including," and "includes" mean including, but not limited to.

As is to be appreciated by those skilled in the relevant art, orthotic products may be placed under the foot or inside footwear, garments, or other coverings or placed directly over major load-bearing joints such as the ankle, knee, lower back, shoulder, neck, elbow, and other joint area extremities for the purpose of providing improved fit or comfort or structural support to an individual. Examples of orthotic products include insoles; foot cushions; heel cups; ankle braces, wraps, and tapes; knee braces, wraps, and tapes; wrist braces, wraps, and tapes; etc. A consumer may want to quickly and accurately identify the proper orthotic product for their individual physical attributes. For example, a product may need to have the proper support, size, angular characteristics and functionality in connection with a person's weight, height, or other sizing quality. Accordingly, retailers who make orthotic products available to consumers would want to be able to provide such a sizing or custom-fitting service to consumers without having to staff a person that has specialized training and/or knowledge of all possible products and physical attribute.

Example Kiosk

Figure 1:
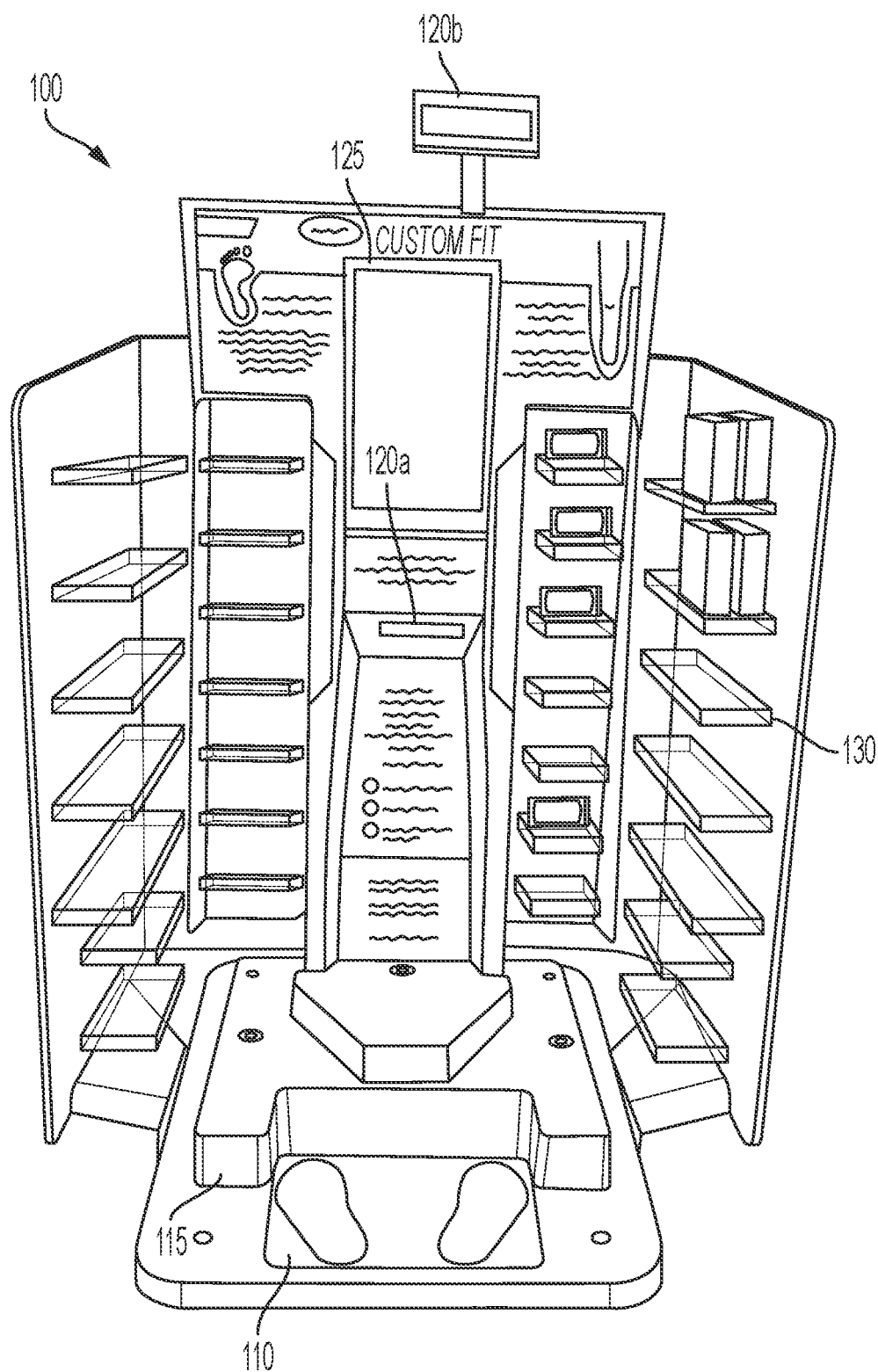
FIG. 1 illustrates an example kiosk that is configured to generate an orthotic product recommendation.

FIG. 1 illustrates an example kiosk 100 that is configured to generate an orthotic product recommendation. The illustrated kiosk 100 includes a foot mat 110, an elevated foot platform 115, imaging sensors 120, a display 125, and shelving 130. Persons of ordinary skill in the art will recognize that many of the items illustrated in FIG. 1 may be optional, such as the shelving. In FIG. 1 and the remaining figures, a letter after a reference number, e.g., "115a," represents a reference to the element having that particular reference number. A reference number in the text without a following letter, e.g., "115," represents a general reference to embodiments of the element bearing that reference number.

The foot mat 110 may include one or more pressure sensors that detect a user that has stepped onto the foot mat 110 and pressure points of the user's feet. The foot mat 110 may also be configured to transmit data used by a kiosk application to determine characteristics of the user's feet including foot length, foot geometry, etc. The foot mat 110 may transmit data used by a kiosk application to determine a contact width and contact length of one or more feet placed on the foot mat 110. As discussed below, the contact width and contact length may be used to estimate an arch measurement of the foot of the user. The foot mat may be configured to determine characteristics of the user including the user's weight. The foot mat may have an outline of feet or a depressed area for the feet to advantageously constrict a position of the user so that the scan data is accurate. In some embodiments, the foot mat 110 positions a user to be about 42 inches from the lower imaging sensor 120a.

The elevated foot platform 115 may be provided to facilitate the positioning of the one or more extremity areas of interest within the field of view of the one or more imaging sensors 120, or to allow a wide field of view imaging system to prioritize analysis of the proper extremity and/or joint of interest. The elevated foot platform 115 may be stationary or movable by mechanical means to provide fine tuning for the positioning of the extremity area of interest relative to the field of view of the one or more imaging sensors 120. For example, the elevated foot platform 115 may be provided that, upon the user placing a foot on the elevated foot platform 115, the ankle is positioned within the field of view of the lower imaging sensor 120a. Alternatively, multiple platforms may be provided, or a platform may be of adjustable height by manual or mechanical means, wherein the mechanical means is controlled by a kiosk application and the fine tuning adjustment is based on a model of an extremity area of interest.

In the illustrated embodiment, the elevated foot platform 115 includes depressions in a plastic cover that guide the user in a proper position on the elevated foot platform 115. The elevated foot platform 115 may include a left depression for a left foot, a right depression for a right foot, and a center depression for the foot that corresponds to a leg that is being fitted for an orthotic product. For example, if the user is looking to receive a recommendation for an ankle brace for the user's left ankle, the user may place the user's left ankle in the center depression. The kiosk 100 may include one or more imaging sensors 120. The one or more imaging sensors 120 may be depth-sensing cameras (e.g., the Microsoft Kinect V2) that operate in one or more modes, including infrared imaging, range imaging, ultrasound imaging, or any other mechanism known in the art that uses backscatter data to determine the relative distance and characteristics of a targeted area. For example, the imaging sensors 120 may measure the time-of-flight for a laser pulse to leave each of the imaging sensors 120 and reflect back onto the focal plane array. The imaging sensors 120 may generate scan data that represents two-dimensional (2D) images that are each a sagittal slice of one or more extremities of interest. The scan data captured by the one or more imaging sensors 120 may be used by a kiosk application to determine a model of one of more extremities of the user.

The one or more imaging sensors 120 may be configured to pivot or slew as needed to include the extremity of interest in its field of view. The one or more imaging sensors may further be positioned at any location such that the extremity area of interest can be put in its field of view by asking the user to move back from or towards the one or more imaging sensors 120. The one or more imaging sensors 120 may be provided with a wide field of view and/or may be configured to mechanically pivot or slew to encompass a different field of view relative to its initial location.

In this embodiment, the kiosk 100 includes a lower imaging sensor 120a and an upper imaging sensor 120b. The lower imaging sensor 120a may be positioned at a location relative to the average knee height (or average height/location of a different area of interest for an extremity) of the potential user population such that the knee or other relevant area of a lower extremity is within the field of view of the lower imaging sensor 120a. In some embodiments, the lower imaging sensor 120a may be at a fixed location relative to the average pelvis height of the potential user population. The lower imaging sensor 120a may be positioned to capture scan data of a user's 125 lower extremities, such as the user's waist, knees, ankle, feet, etc.

The upper imaging sensor 120b may be positioned at a location above the user's 125 head. The upper imaging sensor 120b may capture scan data of a user's 125 upper extremities, such as the user's neck, chest, elbows, wrists, etc. The upper imaging sensor 120b may be used to determine the height of the user.

In some embodiments, each of the lower imaging sensor 120a and the upper imaging sensor 120b may operate independently to provide input to the kiosk application 203, or as a combination of imaging sensors 120 to provide multiple inputs from different vantage points relative to one or more extremity areas of interest as multiple input sources to the kiosk application 203. One or more of the imaging sensors 120 may be configured for the purpose of assisting the user in orienting properly on the foot mat 110. Alternatively, the foot mat 110 may include pressure points that detect whether the user is properly oriented on the foot mat 110.

The kiosk 100 may include a display 125 configured to present visual cues, interactions, instructions, images, image sensor feeds, extremity models, and user input requests to the user. In some embodiments the display 125 may be capacitive touch interface or other device as are known in the art to be capable of both displaying content and receiving user input, such as a touch-screen display. In some embodiments, the display 125 may perform voice recognition and interact with the user based on a series of audio commands. Other input mechanisms may be used as well, for example, a keyboard, mouse, stylus, non-contact gesture control, or other similar interface device may be used. The display may be configured to request information from the user, instruct the user to move into certain positions, and recommend one or more orthotic products to the user.

The kiosk 100 may include shelving 130 that holds orthotic products. In some embodiments, the kiosk 100 measures a user's one or more extremities and generates an orthotic product recommendation that may be stored in the shelving 130 of the kiosk 100. The display 125 may include an indicia of the recommended orthotic product, such as a picture of the orthotic product, the model number of the orthotic product, a color symbol, shelf location, etc. The user may then easily locate the orthotic product that will provide the best calculated fit and support the user's need in accordance with the user's physical attributes as calculated based on the inputs provided and/or detected.

Alternatively, the orthotic product may be dispensed from the kiosk 100. For example, the kiosk 100 may be configured as a vending machine. The orthotic product sold may be a pre-manufactured orthotic, and the set of candidate orthotic products may be a set of different models of pre-manufactured orthotics of varying attributes, such as type of orthotic product, size, arch support levels, arch index, cushioning levels (e.g., foam density, cushioning material used, etc.), etc. The range of models provided may be chosen to address common conditions needing an orthotic product, and in range of sizes and models needed to fit and provide an appropriate support level for the potential user population.

In some embodiments, such as where the user's physical attributes correspond to an orthotic product that is not available at the retail location or one that is not within the set of those appropriate for a particular user location, the display 125 may include information for obtaining the orthotic product from a different source. For example, the kiosk 100 may access a network to request that a conforming orthotic product be manufactured in accordance with the physical attributes of the user, to identify other sales locations at which that particular orthotic product is available, or to email the details of the recommended orthotic product to the user.

Example System

Figure 2:
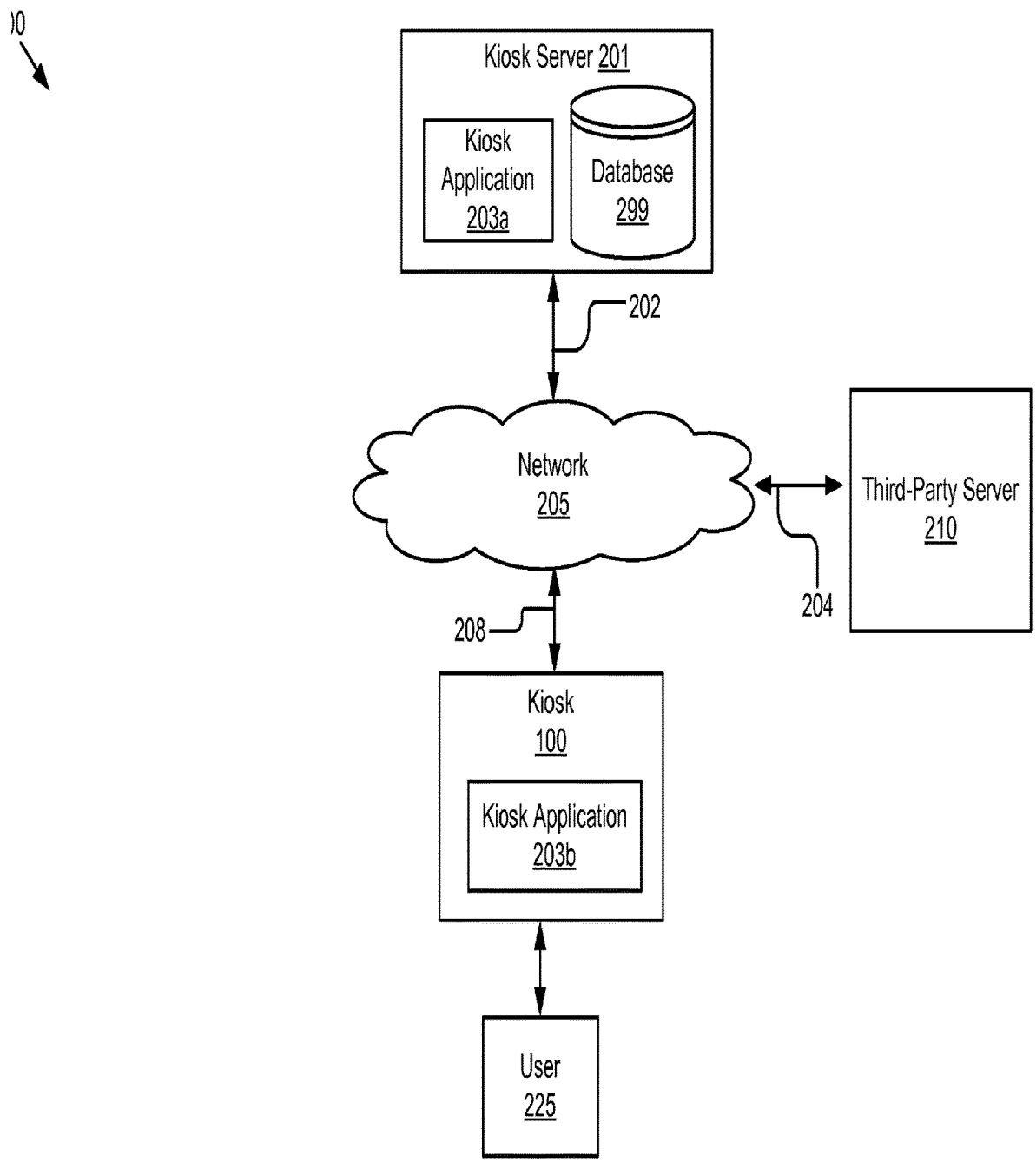
FIG. 2 illustrates a block diagram of an example system that generates an orthotic product recommendation.

FIG. 2 illustrates a block diagram of an example system 200 that generates orthotic product recommendations for users. The illustrated system 200 includes a kiosk server 201, a kiosk 100, a third-party server 210, and a network 205.

The kiosk server 201 may include a processor, a memory and network communication capabilities. In some embodiments, the server 201 is a hardware server 201. The server 201 is communicatively coupled to the network 205 via signal line 202. Signal line 202 may be a wired connection, such as Ethernet, coaxial cable, fiber-optic cable, etc., or a wireless connection, such as Wi-Fi, Bluetooth, or other wireless technology.

In some embodiments, the kiosk server 201 sends and receives data to and from the kiosk 100 via the network 205. The kiosk server 201 may include a kiosk application 203a and a database 299. The kiosk server 201 may receive a request from the kiosk application 203b stored on the kiosk 100 to perform some additional processing. For example, in some embodiments the kiosk application 203a on the kiosk server 201 receive measurements for a user 225 and generates a model one or more extremity areas of the user 225. The kiosk application 203a may receive template data including one or more template models from the database 299 and compare the measurements of the user 225 to the template data to generate the model for the user 225. In some embodiments, the kiosk application 203a may include the template data and perform comparisons with the template data.

The kiosk 100 includes a kiosk application 203b that may be code and routines configured to generate an orthotic product recommendation for a user 225. In some embodiments, the kiosk application 203b may be implemented using hardware including a field-programmable gate array (FPGA) or an application-specific integrated circuit (ASIC). In some embodiments, the kiosk application 203b may be implemented using a combination of hardware and software. In the illustrated embodiment, the kiosk 100 is coupled to the network 205 via signal line 208. Signal lines 208 may be a wired connection, such as Ethernet, coaxial cable, fiber-optic cable, etc., or a wireless connection, such as Wi-Fi, Bluetooth, or other wireless technology. The kiosk 100 and the user 225 in FIG. 1 are used by way of example. While FIG. 1 illustrates one kiosk 100 and one user 225, the disclosure applies to a system architecture having one or more kiosks 100 and one or more users 125.

The third-party server 210 may include a processor, a memory and network communication capabilities. The third-party server 210 may be configured to send data to and from the kiosk 100 and/or the kiosk server 201. For example, the third-party server 210 may include an application configured to determine a stock of orthotic products in one or more physical stores or other kiosks 100. In another example, the third-party server 210 may include an application configured to order a custom-made orthotic product for the user 225. The third-party server 210 may communicate with the network 205 via signal line 204.

In the illustrated implementation, the entities of the system 200 are communicatively coupled via a network 205. The network 205 may be a conventional type, wired or wireless, and may have numerous different configurations including a star configuration, token ring configuration or other configurations. Furthermore, the network 205 may include a local area network (LAN), a wide area network (WAN) (e.g., the Internet), and/or other interconnected data paths across which multiple devices may communicate. In some embodiments, the network 205 may be a peer-to-peer network. The network 205 may also be coupled to or include portions of a telecommunications network for sending data in a variety of different communication protocols. In some embodiments, the network 205 includes Bluetooth® communication networks or a cellular communications network for sending and receiving data including via short messaging service (SMS), multimedia messaging service (MMS), hypertext transfer protocol (HTTP), direct data connection, wireless application protocol (WAP), email, etc. Although FIG. 2 illustrates one network 205 coupled to the kiosk 100, the kiosk server 201, and the third-party server 210, in practice one or more networks 205 may be coupled to these entities.

Example Computing Device

Figure 3:
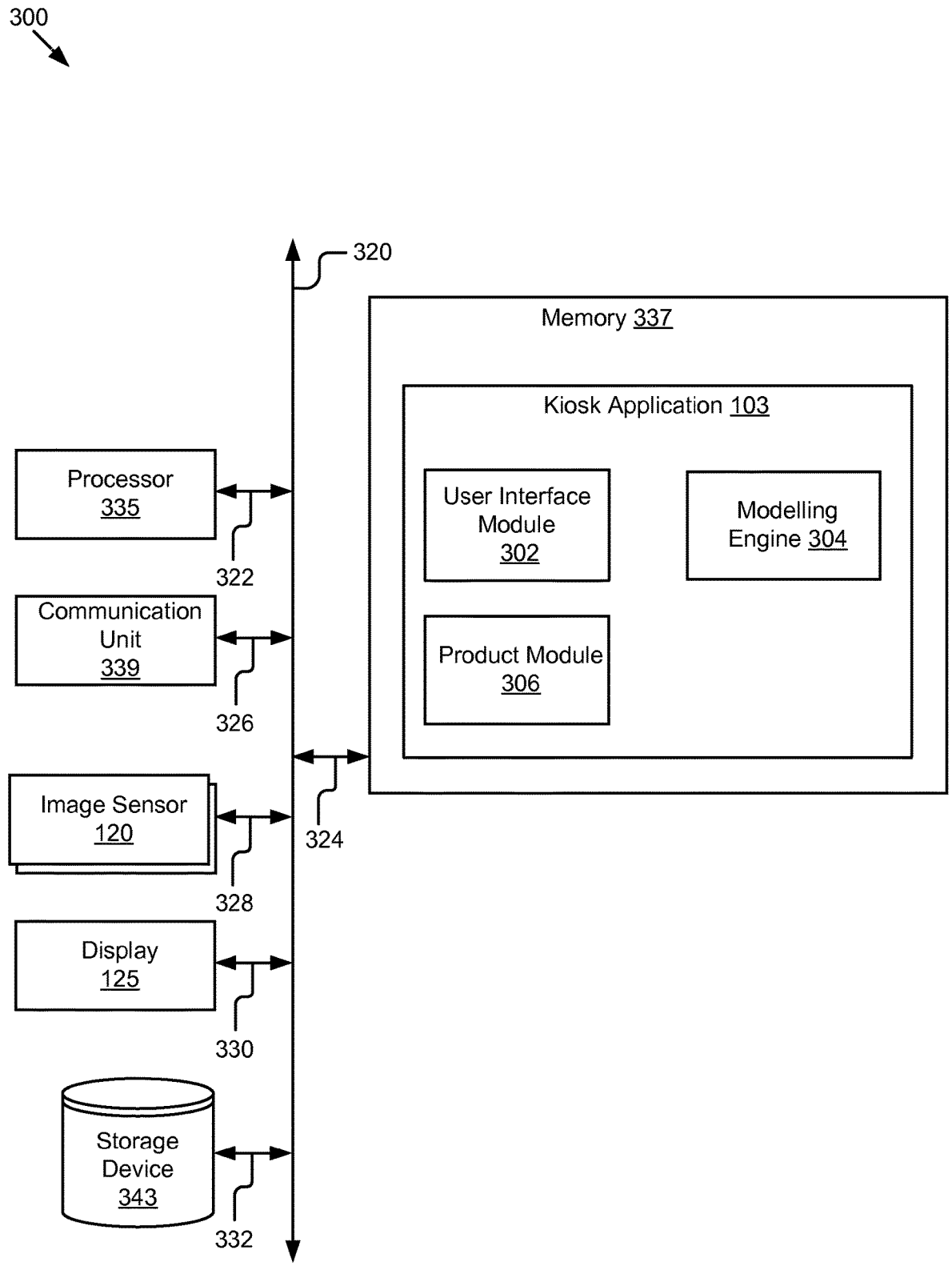
FIG. 3 illustrates a block diagram of an example computing device that generates an orthotic product recommendation.

FIG. 3 illustrates a block diagram of an example computing device 300 that generates an orthotic product recommendation. The computing device 300 may be a kiosk server 201 or a kiosk 100. Although the components of the kiosk application 203 are illustrated as being included on a single computing device 300, persons of ordinary skill in the art will recognize that the kiosk application 203 could be stored in part on a first computing device 300 (e.g., the kiosk server 201) and in part on a second computing device 300 (e.g., the kiosk 100). The computing device 300 may include a processor 335, a memory 337, a communication unit 339, one or more imaging sensors 120, a display 125, and a storage device 343. In embodiments where the kiosk application 203 is stored on the kiosk server 201, some of the components may not be included, such as the imaging sensor 120 and the display 125. The components of the computing device 300 may be communicatively coupled by a bus 320.

The processor 335 includes an arithmetic logic unit, a microprocessor, a general purpose controller or some other processor array to perform computations and provide instructions to a display device. Processor 335 processes data and may include various computing architectures including a complex instruction set computer (CISC) architecture, a reduced instruction set computer (RISC) architecture, or an architecture implementing a combination of instruction sets. Although FIG. 3 includes a single processor 335, multiple processors 235 may be included. Other processors, operating systems, sensors, displays and physical configurations may be part of the computing device 300. The processor 335 is coupled to the bus 320 for communication with the other components via signal line 322.

The memory 337 stores instructions that may be executed by the processor 335 and/or data. The instructions may include code for performing the techniques described herein. The memory 337 may be a dynamic random access memory (DRAM) device, a static RAM, or some other memory device. In some embodiments, the memory 337 also includes a non-volatile memory, such as a (SRAM) device or flash memory, or similar permanent storage device and media including a hard disk drive, a floppy disk drive, a compact disc read only memory (CD-ROM) device, a DVD-ROM device, a DVD-RAM device, a DVD-RW device, a flash memory device, or some other mass storage device for storing information on a more permanent basis. The memory 337 includes code and routines configured to execute the kiosk application 203, which is described in greater detail below. The memory 337 is coupled to the bus 320 for communication with the other components via signal line 324.

The communication unit 339 transmits and receives data to and from at least one of the kiosk 100 and the server 201 depending upon where the kiosk application 203 may be stored. In some embodiments, the communication unit 339 includes a port for direct physical connection to the network 205 or to another communication channel. For example, the communication unit 339 includes a universal serial bus (USB), secure digital (SD), category 5 cable (CAT-5) or similar port for wired communication with the kiosk 100 or the server 201, depending on where the kiosk application 203 may be stored. In some embodiments, the communication unit 339 includes a wireless transceiver for exchanging data with the kiosk 100, server 201, or other communication channels using one or more wireless communication methods, including IEEE 802.11, IEEE 802.16, Bluetooth® or another suitable wireless communication method. The communication unit 339 is coupled to the bus 320 for communication with the other components via signal line 326.

In some embodiments, the communication unit 339 includes a cellular communications transceiver for sending and receiving data over a cellular communications network including via short messaging service (SMS), multimedia messaging service (MMS), hypertext transfer protocol (HTTP), direct data connection, WAP, e-mail or another suitable type of electronic communication. In some embodiments, the communication unit 339 includes a wired port and a wireless transceiver. The communication unit 339 also provides other conventional connections to the network 205 for distribution of files and/or media objects using standard network protocols including, but not limited to, UDP, TCP/IP, HTTP, HTTPS, SMTP, SPDY, QUIC, etc.

The imaging sensors 120 may be depth sensors that are configured to capture scan data that is transmitted to the kiosk application 203. Additional details of the imaging sensors 120 may be found above with reference to FIG. 1. The imaging sensors 120 are coupled to the bus 320 via signal line 328.

The display 125 may include hardware configured to display graphical data received from the kiosk application 203. For example, the display 125 may render graphics to display a user interface that is configured to display an orthotic produce recommendation. The display 125 is coupled to the bus 320 for communication with the other components via signal line 330.

Other hardware components that provide information to a user may be included as part of the computing device 300. For example, the computing device 300 may include a speaker for audio interfaces or other types of non-display output devices. In some embodiments, such as where the computing device 300 is a server 201, the display 125 may be optional. In some embodiments, the computing device 300 may not include all the components. In some embodiments, the computing device 300 may include other components not listed here, e.g., sensors, a battery, etc.

The storage device 343 may be a non-transitory computer-readable storage medium that stores data that provides the functionality described herein. In embodiments where the computing device 300 is the server 201, the storage device 343 may include the database 199 in FIG. 1. The storage device 343 may be a DRAM device, a SRAM device, flash memory or some other memory device. In some embodiments, the storage device 343 also includes a non-volatile memory or similar permanent storage device and media including a hard disk drive, a floppy disk drive, a CD-ROM device, a DVD-ROM device, a DVD-RAM device, a DVD-RW device, a flash memory device, or some other mass storage device for storing information on a permanent basis. The storage device 343 is coupled to the bus 320 for communication with the other components via signal line 332.

In the illustrated implementation shown in FIG. 3, the kiosk application 203 includes a user interface module 302, a modelling engine 304, and a product module 306. Other modules and/or configurations are possible.

The user interface module 302 may be configured to provide and receive information to and from a user. In some embodiments, the user interface module 302 can be a set of instructions executable by the processor 335 to provide the functionality described below for providing and receiving information to and from a user. In some embodiments, the user interface module 302 can be stored in the memory 337 of the computing device 300 and can be accessible and executable by the processor 335.

In some embodiments, the user interface module 302 generates a user interface to interact with a user. The user interface may display data relating to multiple stages. For example, the stages may include an introduction stage, an about the user stage, an about the concern area stage, a scanning stage, and a product recommendation stage. The introduction stage may include a default screen that describes the purpose of the kiosk and the technology used to recommend one or more orthotic products.

The user interface for the introduction stage may include information for the purpose of capturing a user's attention as a marketing or advertising mechanism. For example, the user interface module 302 may receive scan data from one or more image sensors 120 and generate a full-body image of the user upon which one or more orthotic products may be overlayed.

The user interface for the introduction stage may include a start button to move on to another stage. The user interface may also include a request that the user remove the user's shoes. The about the user stage may include a user interface that requests information about the user, such as the gender of the user and an identification of the user's clothing. The identification of the user's clothing may be used later in the program to provide more specific instructions, such as "Please roll up your pant leg to expose your knee" or "Please pull up your skirt to expose your knee."

The user interface module 302 may also generate a user interface that asks the user to identify one or more extremity areas of interest. For example, the user interface may include a diagram of a body and instructions that the user select areas of the body on the diagram that are of concern to the user. In some embodiments the user interface module 302 may ask the user to input the user's height and weight.

The about the concern area stage may include a user interface that requests information about the one or more extremity areas of interest. For example, the questions may include symptoms associated with the one or more extremity areas of interest and how frequently the one or more extremity areas of interest are used. The user interface may include a question about whether a problem associated with the one or more extremity areas of interest arose from an injury, a level of pain associated with the problem, an ability to stretch the one or more extremities, comfort parameters, whether there is swelling, the user's activity level, and what activities the user might perform while wearing one or more orthotic products. The user interface may include follow up questions if the problem associated with the one or more extremity areas of interest arose from an injury, such as a length of time associated with the injury and whether the injury is recurring.

The questions may be tailored to the type of extremity area. For example, if the extremity area of interest is a foot, the question may be about the type of footwear used by the user, whether the user has tried different types of insoles, etc. If the extremity area of interest is an ankle or a knee, the questions may include clarification of impact levels.

The scanning stage may include a user interface that provides the user with scan instructions. For example, the instructions may include asking the user to remove the user's shoes (e.g., if this was not done earlier), expose the one or more extremities if the user is wearing a garment that covers the one or more extremities, and step up on the foot mat or the elevated foot platform. Because the garments may prevent the modelling engine 304 from determining a location of the user's knee and/or extrapolate the true physical attributes of the extremity of interest, it is important that the user remove any garments covering the knee.

In some embodiments, the scanning stage may include the display of instructional videos. The instructional videos may include a video to show the user how to roll up the user's pants to leave the user's knee unobstructed, a video to show how to step up onto the foot mat or the elevated foot platform, and a video to show how to step down from the foot mat or the elevated foot platform. In some embodiments, the instructional videos may include different versions based on an issue associated with the user. For example, if the user is having trouble properly positioning her foot in the central depression of the elevated foot platform, the user interface module 302 may generate a video to show the user how to position her foot in the central depression. In some embodiments, the instructional videos may be different depending on the gender or age of the user. In some embodiments, during the scanning stage the user interface module 302 may generate a three-dimensional (3D) model of the user's scan data.

In some embodiments, the user interface module 302 may receive scan data from one or more imaging sensors 120 and generate a real-time image or video of the user to assist the user in proposer positioning on or relative to the kiosk. The user interface module 302 may generate a user interface that includes a pre-written script to assist the user in orienting his- or herself on a foot mat and/or an elevated foot platform.

The product recommendation stage may include a user interface that provides scan results and detailed information about the one or more orthotic products. For example, the scan results may include a color map of the pressure points in the user's feet and/or a point cloud of the user's leg. The user interface may also provide a link to an online product purchase website and/or an option for the user to send an email to him- or herself about the one or more orthotic products.

The modelling engine 304 may be configured to generate a model. In some embodiments, the modelling engine 304 may be a set of instructions executable by the processor 335 to generate the model. In some embodiments, the modelling engine 304 may be stored in the memory 337 of the computing device 300 and can be accessible and executable by the processor 335.

The modelling engine 304 may determine information about the user based on user input and/or sensor data. For example, the modelling engine 304 may determine the user's body mass index (BMI) based on the user's height as determined by the upper imaging sensor and the user's weight as determined by the foot mat. Alternatively, the user may provide the BMI or the user's height and weight via a user interface. The BMI may be used by the product module 308 as a factor in selection of a recommended orthotic product to the user. The modelling engine 304 may determine the user's foot size based on sensor data received from the foot map. The modelling engine 304 may determine the ankle width and knee width based on scan data. In some embodiments, the modelling engine 304 determines widths for the partial circumferences based on the scan data. For example, where the extremity area of interest is the knee, the modelling engine 304 determines a knee width five inches above the knee, three inches above the knee, seven inches above the knee, at the knee, three inches below the knee, five inches below the knee, and seven inches below the knee. In another example, where the extremity area of interest is the ankle, the modelling engine 304 determines an ankle width three inches above the malleolus (i.e., the ankle bone), one inch above the malleolus, at the malleolus, one inch below the malleolus, and three inches below the malleolus.

In some embodiments, the modelling engine 304 receives scan data from one or more image sensors 120 and determines whether the scan data is useable or if the user needs to make a modification. The modelling engine 304 may generate a three-dimensional model, such as a point cloud of the leg and compare the point cloud to template models. In some embodiments, the point cloud is also used to generate the model as discussed below. In some embodiments, the modelling engine 304 generates a different point cloud as part of generating the model.

In some embodiments, the modelling engine 304 receives the scan data and generates a point cloud of the leg from the scan data. The modelling engine 304 may use the point cloud to determine whether the correct leg is being scanned. For example, the modelling engine 304 may determine whether the leg is a right leg or a left leg based on comparing the point cloud to a template model. If the identified leg is different from the leg that the user identified as having one or more extremity areas of interest, the modelling engine 304 may instruct the user interface module 302 to notify the user that the wrong leg was used.

The modelling engine 304 may use the point cloud to determine whether the knee is visible. For example, the modelling engine 304 may determine whether the user is wearing clothing that has wrinkles that interfere with measuring the knee based on: gaps in the contour of the leg, irregular spikes in the contour of the leg, a gradient of contour is beyond a threshold, and/or a length of the contour is below a minimum possible length or beyond a maximum length defined for that location on the leg. If the knee is not visible, or the clothing is not sufficiently smooth or tight, the modelling engine 304 may instruct the user to roll up the user's pant leg or perform other corrective action. In some embodiments, the modelling engine 304 determines whether the knee is visible based upon color, patterns, irregular shape, user input, or an irregular slope.

The modelling engine 304 may use the point cloud to determine whether the leg is in an acceptable position. For example, the modelling engine 304 may compare the point cloud to a template model to determine whether the leg is in an acceptable position. If the leg is in an unacceptable position, the modelling engine 304 may determine a modification that would correct the issue. For example, the modelling engine 304 may instruct the user interface module 302 to make a change, such as leaning right, leaning left, leaning forward, or leaning back.

The modelling engine 304 may generate a model of one or more extremity areas. In some embodiments, the modelling engine 304 performs point-cloud segmentation to divide the scan data into regions of interest known as point clusters. The regions of interest may include a left foot, a right foot, a general knee area, a general hip area, and a general ankle area. For each of the point clusters, the modelling engine may identify a point-cluster centroid and based on the point cluster centroid, identify the locations of skeletal bones and joints in the leg. In some embodiments, the modelling engine may identify joints by estimating substantially perpendicular lines between the locations of the skeleton bones.

The modelling engine 304 may generate a two-dimensional (2D) depth map of the leg from the scan data based on the location of the joints in the leg. In some embodiments, the 2D depth map may be a 2D color map that illustrates different depths of the leg with different colors at discreet locations. The 2D color map advantageously illustrates a representation of the curvature of the leg when bent. The 2D color map may be used to determine the location of the leg to ensure reproducible locations of measurement.

The modelling engine 304 may generate a point cloud of the leg from the 2D depth map where the point cloud represents three-dimensional (3D) unstructured points that form the leg.

The modelling engine 304 may determine one or more partial circumferences that correspond to one or more points of the leg from the 3D scan. A partial circumference is a partial contour that may include a portion of a complete circumference that is visible from the scan data. One advantage to determining multiple partial circumferences, is that the multiple partial circumferences determined above the knee may be used to account for misleading data, such as wrinkles in the user's clothing. In some embodiments, where the orthotic product is for a knee, the modelling engine 304 may determine three partial circumferences up to five inches above the knee and three partial circumferences five inches below the knee. For example, the modelling engine 304 may determine the partial circumference seven inches above the knee, five inches above the knee, three inches above the knee, at the knee, three inches below the knee, five inches below the knee, and seven inches below the knee. In some embodiments, where the orthotic product is for an ankle, the modelling engine 304 may determine one partial circumference up to three inches above the ankle bone, one partial circumference up to one inch above the ankle bone, and one partial circumference at the ankle bone. For example, the modelling engine 304 may determine the partial circumference three inches above the malleolus, one inch above the malleolus, at the malleolus, one inch below the malleolus, and three inches below the malleolus.

The modelling engine 304 may determine one or more complete circumferences based on the one or more partial circumferences. A complete circumference is a complete contour that may include all points of a circumference where the points that are missing from the partial circumference are determined. For example, the modelling engine 304 may estimate the missing points of the partial circumference using regression correlations. The one or more complete circumferences may have an ovoid shape.

In some embodiments, the modelling engine 304 crops the point cloud to identify the knee as being the mid area of the point cloud. The modelling engine 304 may further refine the point cloud by analyzing data in smaller subsections to estimate the complete circumference. In some embodiments, the modelling engine 304 determines whether to analyze smaller subsections based on the sizing of the circumference and the slope of the lines between the locations of the skeleton bones. The modelling engine 304 may also remove noise from the point cloud based on comparing the point cloud to a template model and identifying outliers.

The modelling engine 304 determines the one or more complete circumferences by mirroring the shape of the backside based on a template model of the shape of a leg and the location of the circumference. For example, if the partial circumference is below the knee, the modelling engine 304 may estimate an elongated shape to generate the complete circumference.

The product module 306 may be configured to identify one or more orthotic products for the user. In some embodiments, the product module 306 may be a set of instructions executable by the processor 335 to identify the one or more orthotic products for the user. In some embodiments, the product module 306 may be stored in the memory 337 of the computing device 300 and can be accessible and executable by the processor 335.

The product module 306 may use different factors to identify one or more orthotic products for the user. For example, where the extremity area is a knee, the product module 306 may use the user's complete circumference at five inches below the knee and the user's BMI to identify the one or more orthotic products. In another example, where the extremity area is an ankle, the product module 306 may use a contact width, a contact length, and an estimated arch measurement to identify the one or more orthotic products. Other factors are possible in determining orthotic products to recommend, such as additional complete circumferences for the knee and/or ankle.

In some embodiments, the orthotic products for a knee may be categorized as extra small, small, small wide, medium, medium wide, large, and large wide. In some embodiments, the orthotic products may be further classified into three product families where small includes extra small, small, and small wide; medium includes medium and medium wide; and large includes large and large wide. The product module 306 may use the following BMI categories as defined by the World Health Organization: very severely underweight, severely underweight, underweight, normal, overweight, obese class I, obese class II, and obese class III.

The product module 306 may determine that the user belongs in one of the small, medium, and large product families based on the measurement of the complete circumference at five inches below the knee. If there is only one product available in the corresponding product family (e.g., the product family for large only includes a large product or only a large product is in stock), the product module 306 may recommend the single product (e.g., the large product). If two products are available in the product family, if the user is in one of the obese BMI categories, the product module 306 may recommend the larger of the two products in the product family (e.g., if the product family for large has large and large wide available, large wide is recommended). If the user is not in one of the obese BMI categories, the product module 306 may recommend the larger of the two products in the product category.

If the user is overweight or obese and the product module 306 recommends a product from the small product family or a product recommendation is not possible, the following options may be available. If the customer is overweight, the product module 306 may recommend the small wide product. If the user is in the obese class I or the obese class II, the product module 306 may recommend the medium product. If the user is in the obese class III, the product module 306 may recommend the medium wide product.

For the options mentioned in the two preceding paragraphs, if three of the recommendations for a single product apply to the user, the product module 306 recommends the product. Otherwise, new scan data may be generated, a new model may be generated, and the product module 306 may perform the steps in the two preceding paragraphs until three recommendations for a single product are identified and the product module 306 may recommend the product. Generating new scan data and the new model may be advantageous to correct for variations, such as the user moving slightly during the scanning. In some implementations, the user is scanned between three and five times to identify the one or more orthotic products.

In some embodiments, the orthotic products for an ankle may be categorized as small, small wide, medium, medium wide, and large. The product module 306 may identify the one or more orthotic products in range by assigning a natural number product recommendation. The natural number product recommendation may be a value from 1 to 5, where small corresponds to 1, small wide corresponds to 2, medium corresponds to 3, medium wide corresponds to 4, and large corresponds to 5.

The product module 306 may determine a floating point product recommendation value using a polynomial regression calculation based on the natural number product recommendation value. The product module 306 may determine an arch measurement for the user based on a contact width value using a polynomial regression calculation, where the resulting value from the polynomial regression calculation is used to determine a contact-width-based floating point product recommendation value. The arch measurement may also be based on a contact length value using a linear regression calculation, where the resulting value from the polynomial regression calculation is used to determine a contact-length-based floating point product recommendation value.

The product module 306 may determine a natural number product recommendation by using a weighted average calculation using weights and rounding the resulting value to the nearest natural number. For example, the weights may include: a natural number product recommendation weight of 0.3, a floating point product recommendation weight of 0.1, a contact-length-based floating point product recommendation weight of 0.3, and a contact-width-based floating point product recommendation weight of 0.3. If the resulting natural number recommendation value is over 5, the value may be set to 5. If the natural number recommendation value is less than 1, the value may be set to 1.

The product module 306 may determine the orthotic product to recommend based on mapping the natural number recommendation value to the integers associated with the orthotic product sizes. For example, if the natural number recommendation value is 3, the product module 306 recommends the medium size.

The product module 306 may instruct the user interface module 302 to display information about the orthotic product as discussed in greater detail above.

Example Methods

Figure 4:
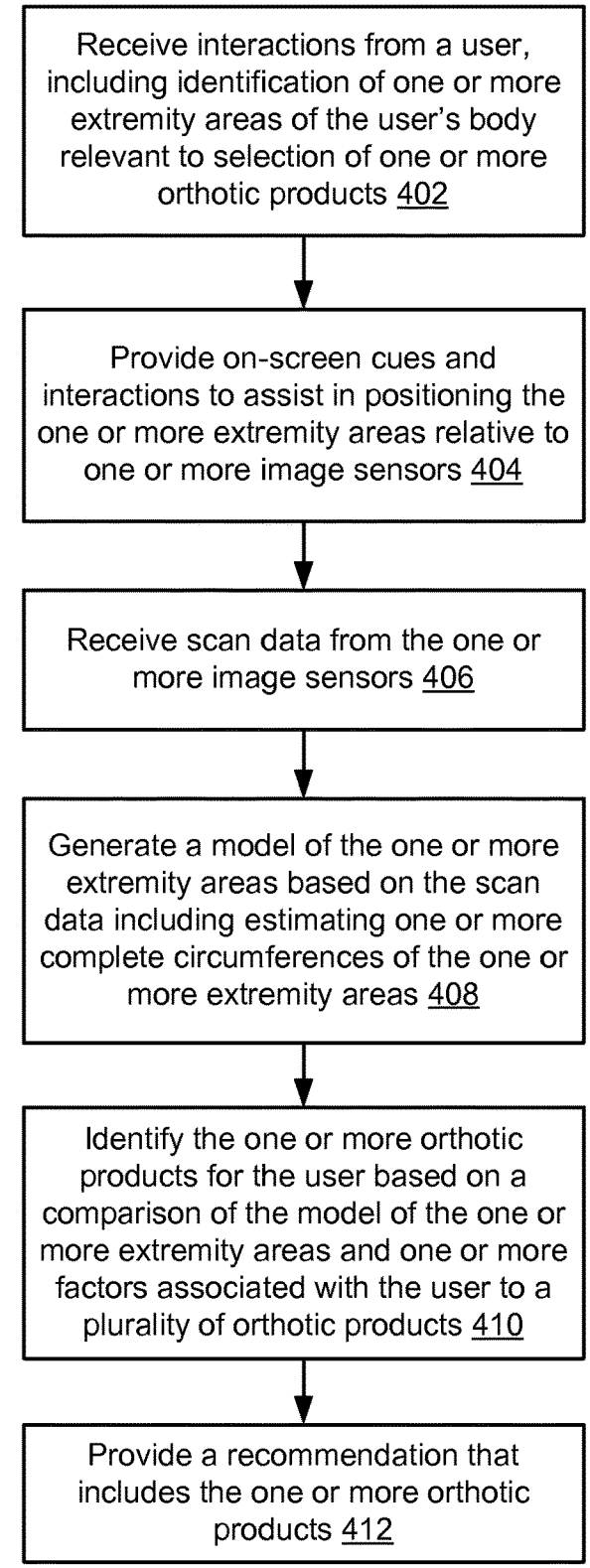
FIG. 4 is a flowchart of an example method to generate an orthotic product recommendation.

FIG. 4 is a flowchart of an example method 400 to generate orthotic product recommendations. The method 400 may be implemented by the kiosk server 201, a kiosk 100 or a combination of the kiosk server 201 and the kiosk 100, in the kiosk application 203 illustrated in FIG. 2.

At block 402, interactions are received from a user including identification of one or more extremity areas of the user's body relevant to selection of one or more orthotic products. At block 404, on-screen cues and interactions are provided to assist in positioning of the one or more extremity areas relative to one or more image sensors. At block 406, scan data is received from the one or more image sensors. At block 408, a model of the one or more extremity areas are generated based upon the scan data including estimating one or more complete circumferences of the one or more extremity areas. At block 410, one or more orthotic products are identified for the user based on a comparison of the model of the one or more extremity areas and one or more factors associated with the user to a plurality of orthotic products. At block 412, a recommendation is provided that includes the one or more orthotic products. While blocks 402 to 412 are illustrated in a particular order, other orders are possible with intervening steps. In some embodiments, some blocks may be added, skipped, or combined.

Figure 5:
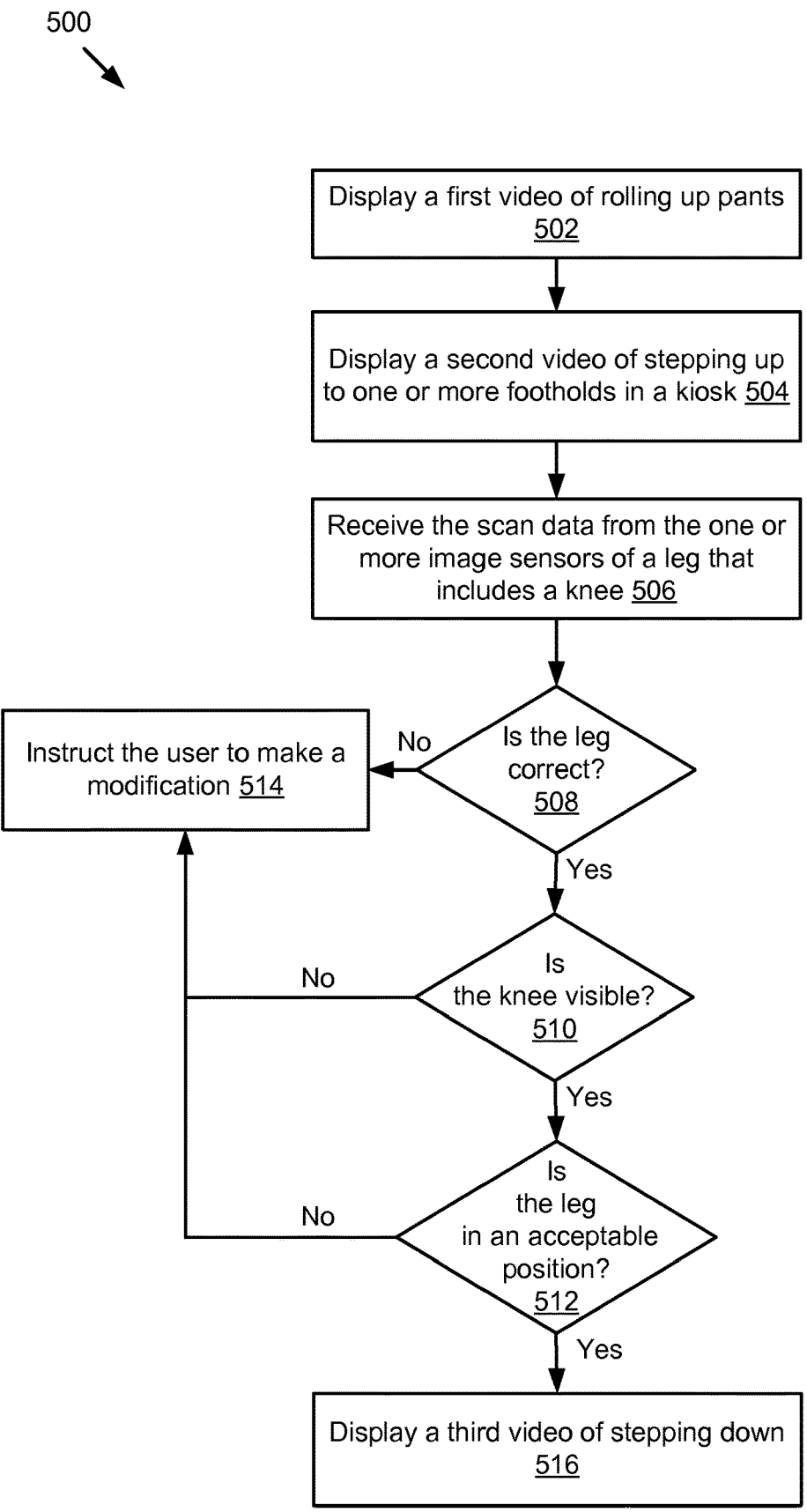
FIG. 5 is a flowchart of an example method to provide the user with on-screen cues and interactions to assist in scanning one or more extremity areas.

FIG. 5 is a flowchart of an example method 500 to provide the user with on-screen cues and interactions to assist in scanning one or more extremity areas. The method 500 may be implemented by the kiosk server 201, a kiosk 100 or a combination of the kiosk server 201 and the kiosk 100, in the kiosk application 203 illustrated in FIG. 2.

At block 502, a first video of rolling up pants is displayed. At block 504, a second video of stepping up to one or more footholds in a kiosk is displayed. At block 506, scan data from the one or more image sensors are received, where the scan data includes a leg that includes a knee. At block 508, it is determined whether the leg is correct. If the leg is correct, the method 500 proceeds to block 510. At block 510, it is determined whether the knee is visible. If the knee is visible, the method 500 proceeds to block 512. At block 512, it is determined whether the leg is in an acceptable position. If the leg is in an acceptable position, a third video of stepping down is displayed. If the leg is not correct, the knee is not visible, and/or the leg is not in an acceptable position, the method 500 proceeds to block 514. At block 514, the user is instructed to make a modification. While blocks 502 to 516 are illustrated in a particular order, other orders are possible with intervening steps. In some embodiments, some blocks may be added, skipped, or combined.

Figure 6:
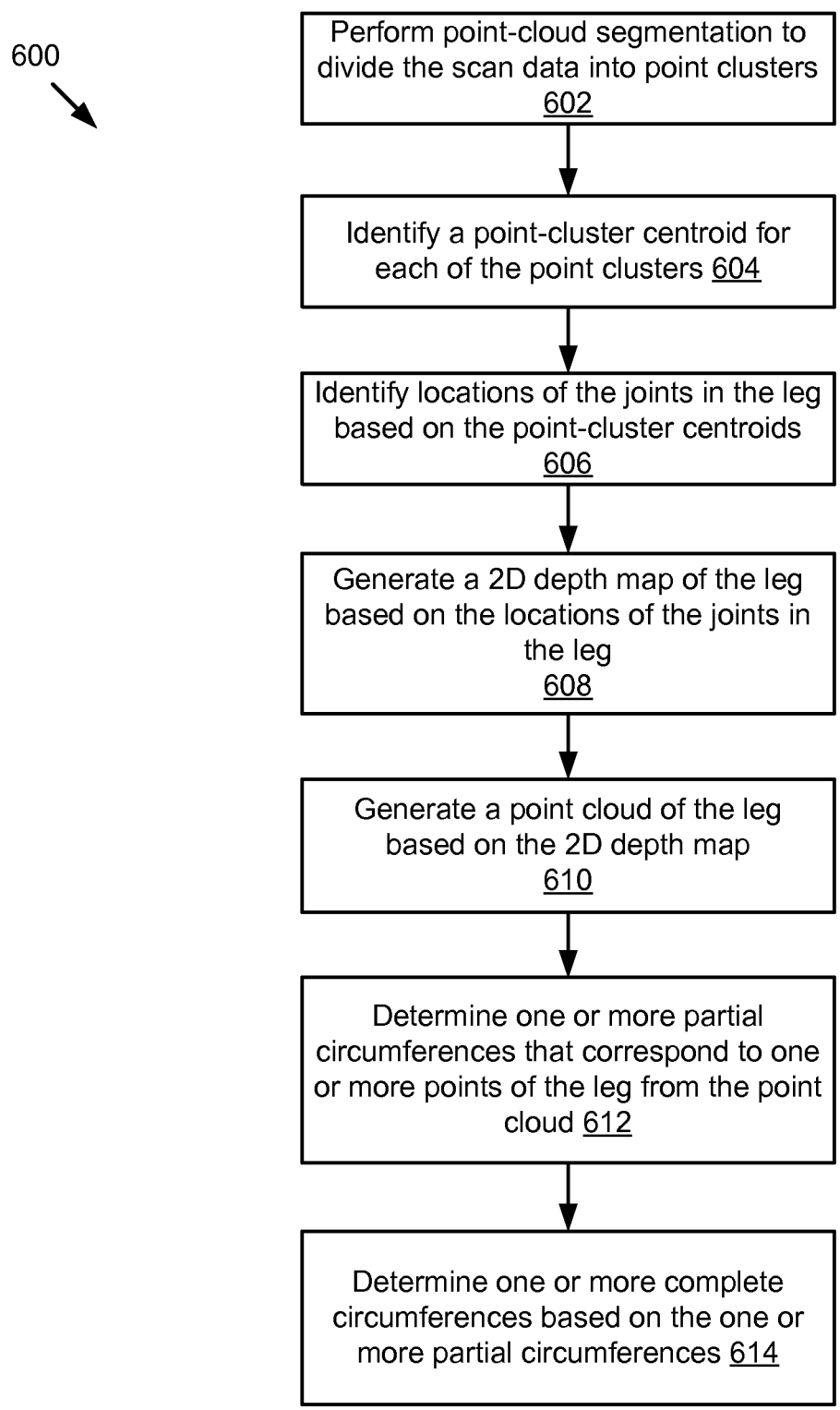
FIG. 6 is a flowchart of an example method to generate a model of the one or more extremity areas.

FIG. 6 is a flowchart of an example method 600 to generate a model of the one or more extremity areas. The method 600 may be implemented by the kiosk server 201, a kiosk 100 or a combination of the kiosk server 201 and the kiosk 100, in the kiosk application 203 illustrated in FIG. 2.

At block 602, point-cloud segmentation is performed to divide the scan data into point clusters. At block 604, a point-cluster centroid is identified for each of the point clusters. At block 606, locations are identified for each of the joints in the leg based on the point-cluster centroids. At block 608, a 2D depth map of the leg is generated based on the locations of the joints in the leg. At block 610, a point cloud of the leg is generated based on the 2D depth map. At block 612, one or more partial circumferences that correspond to one or more points of the leg from the point cloud are determined. At block 614, one or more complete circumferences are determined based on the one or more partial circumferences. While blocks 602 to 614 are illustrated in a particular order, other orders are possible with intervening steps. In some embodiments, some blocks may be added, skipped, or combined.

Example Graphic Representations of Animations

Figure 7:
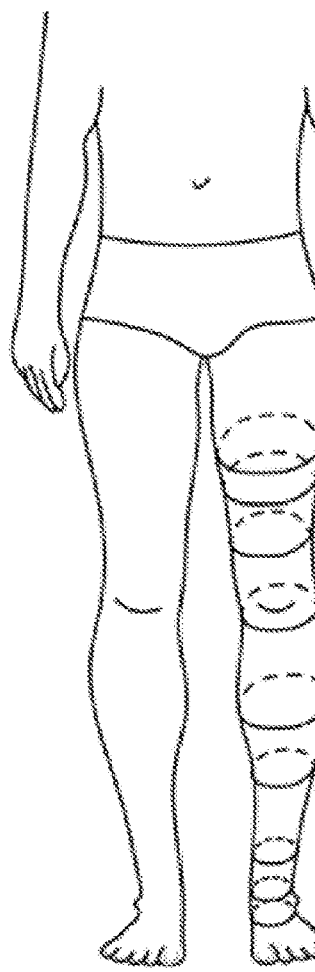
FIG. 7 is an example graphic representation of circumferences estimated for recommending an orthotic product for a knee.

FIG. 7 is an example graphic representation 700 of circumferences estimated for recommending an orthotic product for a knee. In this example, the modelling engine 304 generates circumferences for recommending an orthotic product for a knee and circumferences for recommending an orthotic product for an ankle. For the knee, the modelling engine 304 generates circumferences for seven inches above the knee, five inches above the knee, three inches above the knee, at the knee, three inches below the knee, and five inches below the knee. For the ankle, the modelling engine 304 generates circumferences three inches above the ankle bone, one inch above the ankle bone, and at the ankle bone.

The circumferences are illustrates with solid lines and dashed lines. The solid lines represent the partial circumferences described above with reference to FIG. 6. The dashed lines represent the missing points that are filled in when the modelling engine 304 determines the complete circumferences.

In the above description, for purposes of explanation, numerous specific details are set forth in order to provide a thorough understanding of the specification. It will be apparent, however, to one skilled in the art that the disclosure can be practiced without these specific details. In some instances, structures and devices are shown in block diagram form in order to avoid obscuring the description. For example, the embodiments can be described above primarily with reference to user interfaces and particular hardware. However, the embodiments can apply to any type of computing device that can receive data and commands, and any peripheral devices providing services.

Reference in the specification to "some embodiments" or "some instances" means that a particular feature, structure, or characteristic described in connection with the embodiments or instances can be included in at least one implementation of the description. The appearances of the phrase "in some embodiments" in various places in the specification are not necessarily all referring to the same embodiments.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic data capable of being stored, transferred, combined, compared, and otherwise manipulated. It has proven convenient at times, principally for reasons of common usage, to refer to these data as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms including "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

The embodiments of the specification can also relate to a processor for performing one or more steps of the methods described above. The processor may be a special-purpose processor selectively activated or reconfigured by a computer program stored in the computer. Such a computer program may be stored in a non-transitory computer-readable storage medium, including, but not limited to, any type of disk including floppy disks, optical disks, ROMs, CD-ROMs, magnetic disks, RAMs, EPROMs, EEPROMs, magnetic or optical cards, flash memories including USB keys with non-volatile memory, or any type of media suitable for storing electronic instructions, each coupled to a computer system bus.

The specification can take the form of some entirely hardware embodiments, some entirely software embodiments or some embodiments containing both hardware and software elements. In some embodiments, the specification is implemented in software, which includes, but is not limited to, firmware, resident software, microcode, etc.

Furthermore, the description can take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

A data processing system suitable for storing or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

In situations in which the systems discussed above collect personal information, the systems provide users with an opportunity to control whether programs or features collect user information (e.g., information about a user's social network, social actions or activities, profession, a user's preferences, or a user's current location), or control whether and/or how to receive content from the server that may be more relevant to the user. In addition, certain data may be treated in one or more ways before it is stored or used, so that personally identifiable information is removed. For example, a user's identity may be treated so that no personally identifiable information earl be determined for the user, or a user's geographic location may be generalized where location information is obtained (such as to a city, ZIP code, or state level), so that a particular location of a user cannot be determined. Thus, the user may have control over how information is collected about the user and used by the server.

What is claimed is:

1. A computer-implemented method comprising:
   receiving interactions from a user comprising identification of one or more extremity areas of the user's body, the one or more extremity areas relevant to selection of one or more orthotic products;
   providing on-screen cues and interactions to assist in positioning of the one or more extremity areas relative to one or more imaging sensors;
   receiving scan data from the one or more imaging sensors, the scan data comprising images of a front of the user;
   generating a model of the one or more extremity areas based on the scan data comprising estimating one or more complete circumferences of the one or more extremity areas;
   identifying the one or more orthotic products based on a comparison of the model of the one or more extremity areas and one or more factors associated with the user and a plurality of orthotic products; and
   providing a recommendation that includes the one or more orthotic products.

2. The method of claim 1, wherein estimating the one or more complete circumferences of the one or more extremity areas comprises determining a shape of the one or more extremity areas that is not visible from the images.

3. The method of claim 1, wherein the one or more factors comprises a body mass index of the user.

4. The method of claim 1, wherein providing the on-screen cues and interactions comprises:
   receiving the scan data from the one or more imaging sensors, wherein the scan data is of a leg that includes a knee;
   determining whether the leg is correct;
   responsive to determining that the leg is correct, determining whether the knee is visible; and
   responsive to the knee being visible, determining whether the leg is in a first position.

5. The method of claim 4, further comprising responsive to determining that the leg is incorrect, the knee is not visible, or the leg is in a second position, instructing the user to make a modification.

6. The method of claim 4, wherein the knee is not visible because a garment obstructs part of the knee.

7. The method of claim 1, wherein generating the model of the one or more extremity areas based upon the scan data further comprises:
   performing point-cloud segmentation to divide the scan data into point clusters;
   identifying a point-cluster centroid for each of the point clusters;
   identifying locations of joints in a leg of the user based on the point-cloud centroids;
   generating a two-dimensional depth map of the leg based on the locations of the joints;
   generating a point cloud of the leg based on the two-dimensional depth map;
   determining one or more partial circumferences that correspond to one or more points of the leg from the point cloud; and
   determining the one or more complete circumferences based on the one or more partial circumferences.

8. The method of claim 1, wherein the one or more complete circumferences have an ovoid shape.

9. The method of claim 1, wherein the recommendation is provided to an email address of the user.

\* \* \* \* \*